United States Patent [19]

Olexa

[11] Patent Number: 4,750,506

[45] Date of Patent: Jun. 14, 1988

[54] APPARATUS FOR PROCESSING A SLAB GEL

[76] Inventor: Stephanie A. Olexa, R.D. #4, Landis Mills Road, Bethlehem, Pa. 18015

[21] Appl. No.: 945,823

[22] Filed: Dec. 24, 1986

[51] Int. Cl.$^4$ ............................................. B08B 3/04
[52] U.S. Cl. .................................... 134/201; 134/111; 211/41
[58] Field of Search .................. 134/111, 147, 166 R, 134/169 R, 188, 190, 10, 34, 201; 204/182.8; 210/321.1, 433.2; 422/104; 211/41; 206/334, 456, 557, 564; 220/22.3, 85 SP

[56] References Cited

U.S. PATENT DOCUMENTS

| | | | |
|---|---|---|---|
| 3,482,943 | 12/1969 | Csizmas et al. | 204/182.8 |
| 3,534,747 | 10/1970 | Hoefer | 134/111 |
| 3,817,379 | 6/1974 | Zipilivan et al. | 210/321.1 |
| 3,856,656 | 12/1974 | Brink | 204/182.8 |
| 3,930,880 | 1/1976 | Hoefer | 134/111 |
| 4,077,515 | 3/1978 | Shoberg | 206/456 |
| 4,357,174 | 11/1982 | Rushbrook | 134/10 |
| 4,391,689 | 7/1983 | Golias | 204/182.8 |
| 4,555,024 | 11/1985 | Voss et al. | 206/564 |
| 4,635,791 | 1/1987 | Jackson et al. | 206/456 |
| 4,705,056 | 11/1987 | Chu | 134/111 |

FOREIGN PATENT DOCUMENTS 1123129 2/1962 Fed. Rep. of Germany ...... 206/564

Primary Examiner—Harvey C. Hornsby
Assistant Examiner—C. Reinckens

[57] ABSTRACT

An apparatus for staining and destaining one or more slab gels subsequent to electrophoresis comprises a liquid impermeable enclosure having a bottom, a sidewall portion attached to the bottom and a removable top. A plurality of channels are formed in the sidewall portion of the container. At least one and preferably a plurality of cassettes are provided for retaining the slab gels. The cassettes are disposed within the channels. Each cassette comprises a pair of plates that are hinged together at one end and have a lock at the other end to secure the plates together. Each of the plates has a recess therein and a fluid permeable mesh covers each recess to form a slab gel retaining chamber therebetween. Depending upon the fluid used in the container, the slab gels can either be stained or destained. An advantage of the present apparatus is that the slab gels can be removed from the container without having to pour-off the staining or destaining solutions, thus achieving economy of material usage. Additionally, the cassettes protect the slab gels from damage since the slab gels are loosely retained therein and can be transferred from a staining container to a destaining container merely by transferring the cassettes containing the slab gel.

14 Claims, 4 Drawing Sheets

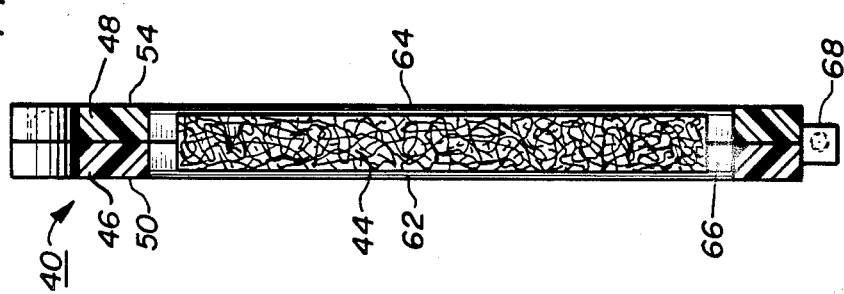
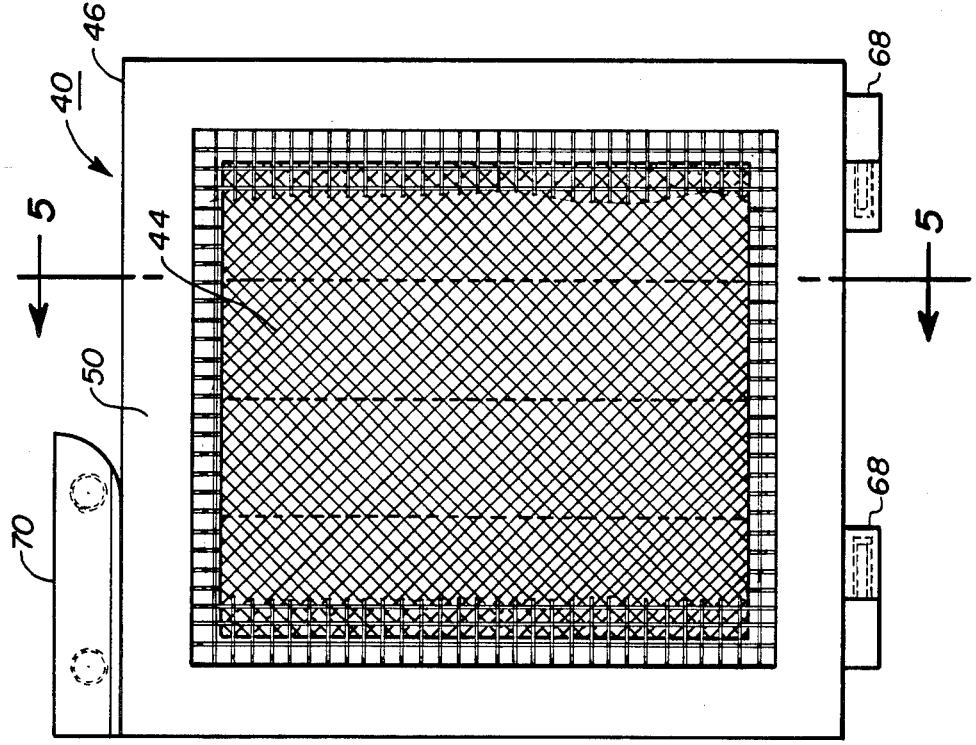

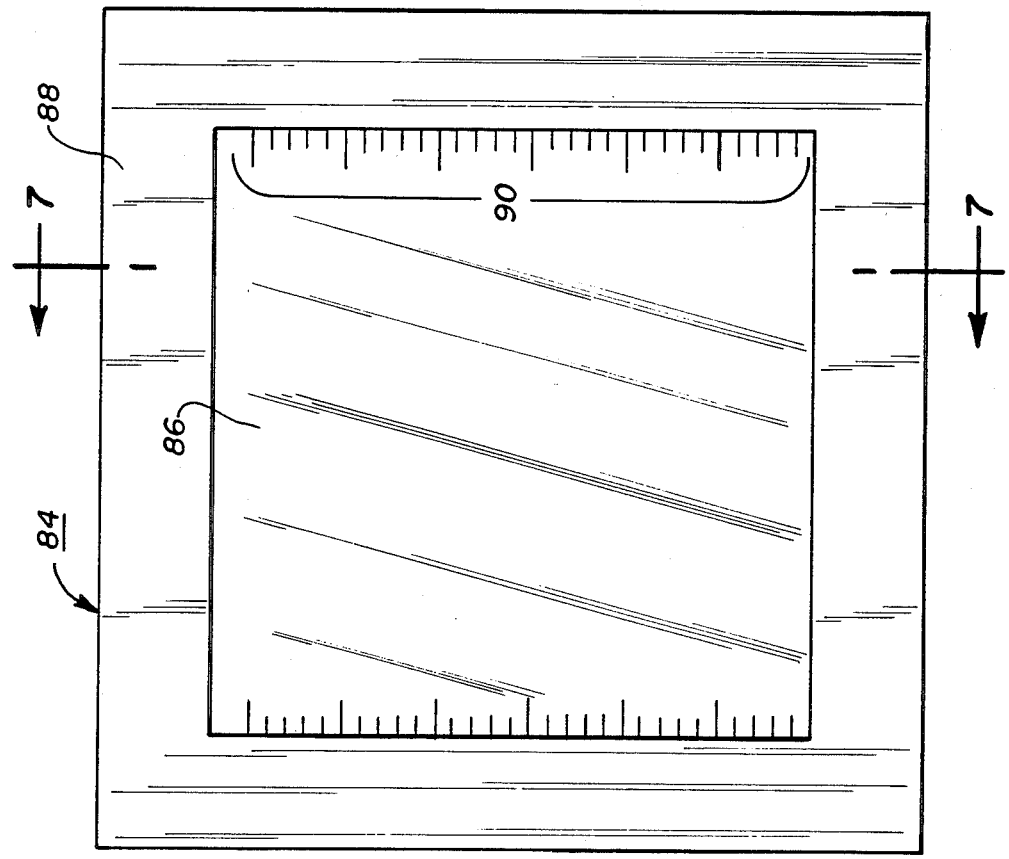

APPARATUS FOR PROCESSING A SLAB GEL

BACKGROUND OF THE INVENTION

The invention relates to an apparatus for processing planar gel layers or slab gels and, more particularly, to an apparatus for staining and destaining electrophoresis slab gels and for examining the destained slab gels.

Electrophoresis is a technique for separating charged molecules of a sample such as protein or DNA on the basis of differences in electrical charge or molecular weight under the influence of an electric field. In general, a polymer material such as polyacrylamide, agar, agarose, or cellulose acetate is used to contain and support the sample. The ionic components of the sample separate or migrate through the support medium (gel) under the influence of the electric field until the elements reach equilibrium. The ionic component separation is not visible to the eye. Consequently, the gel must be stained and fixed with an appropriate stain. The stain permeates the entire gel rendering it a dense opaque color and the surplus stain which is not held by the ionic hands must be removed before the bands themselves become visible. Destaining may be done electrophoretically by passing direct current through the gel or by diffusion. The subsequently destained gel is examined by optical densitometry or other methods, such as photography and can be shrunk and dried for permanent record.

U.S. Pat. No. 4,357,174 issued to Rushbrook et al, on Nov. 2, 1982 discloses a diffusion destainer having a stain absorbing material contained in a hollow housing and disposed within an open, that is topless, destaining container. A drawback of the destaining container is that only a single slab gel can be destained therein. Additionally, the slab is unsupported in the container making handling of the slab difficult during the staining and destaining process. Furthermore, some components of the staining and destaining solutions, such as acetic acid, methanol, ethanol, butanol or isopropanol form vapors which can readily escape from the open container causing an unpleasant and possibly harmful odor.

U.S. Pat. No. 4,391,689 issued to Golias on July 5, 1983 shows an automated electrophoresis and staining apparatus for processing a gel attached to a MYLAR (trademark) sample plate. The sample plate with the gel attached is frictionally supported within a plate holder rack. Gels used in such an apparatus are extremely thin, of the order of a few microns. Such an apparatus is unsuitable for processing gels having a thickness of the order of about 0.4 mm to about 3.0 mm which are not bound to a supportive backing.

U.S. Pat. No. 3,930,880 issued to Hoefer on Jan. 6, 1976 discloses a slab gel diffusion destainer for gels having a thickness in the millimeter range. Subsequent to electrophoresis and staining, the slab gel is supported on a flexible mesh which contacts the slab gel on both sides. The mesh is rolled into a cylindrical form and inserted into a slab holding tube and confined therein by placing end caps on each end of the tube. The tube is disposed within a cylindrical container and a suitable washing liquid is circulated through the interior of the destainer. A problem with this apparatus is that rolling the slab gel in the mesh tends to damage or distort the slab gel. Furthermore, diffusion of the stain into the overlapped portion of the gel can be non-uniform.

With the exception of the destainer described in the above-referenced U.S. Pat. No. 4,357,174, the apparatus described herein are expensive and not well suited for the handling of slab gels.

SUMMARY OF THE INVENTION

An apparatus for processing a slab gel comprises a liquid impermeable enclosure having a bottom, a sidewall portion attached to the bottom and a top. A plurality of indexing means are formed in the sidewall portion. At least one and preferably a plurality of cassettes are provided for retaining the slab gel. The cassettes are disposed within the indexing means. Each cassette comprises a first and a second support plate. Each of the support plates has a first and a second major surface. The support plates are arranged so that the second major surfaces are adjacent to one another. Each of the support plates has a recess formed therein. The first major surface of each support plate includes a liquid permeable membrane, such as a mesh. The membranes extends across the recesses to form a slab gel retaining chamber therebetween. Attachment means are provided for securing said first support plate to said second support plate.

BRIEF DESCRIPTION OF THE DRAWINGS

FIG. 4 is a partially broken-away paln view of a novel cassette retaining a stain absorber.

FIG. 5 is a sectional view taken along line 5—5 of FIG. 4.

FIG. 6 is a plan view of a gel photographic plate according to the present invention.

FIG. 7 is a sectional view taken along line 7—7 of FIG. 6.

DETAILED DESCRIPTION OF THE PREFERRED EMBODIMENT

Figure 1:
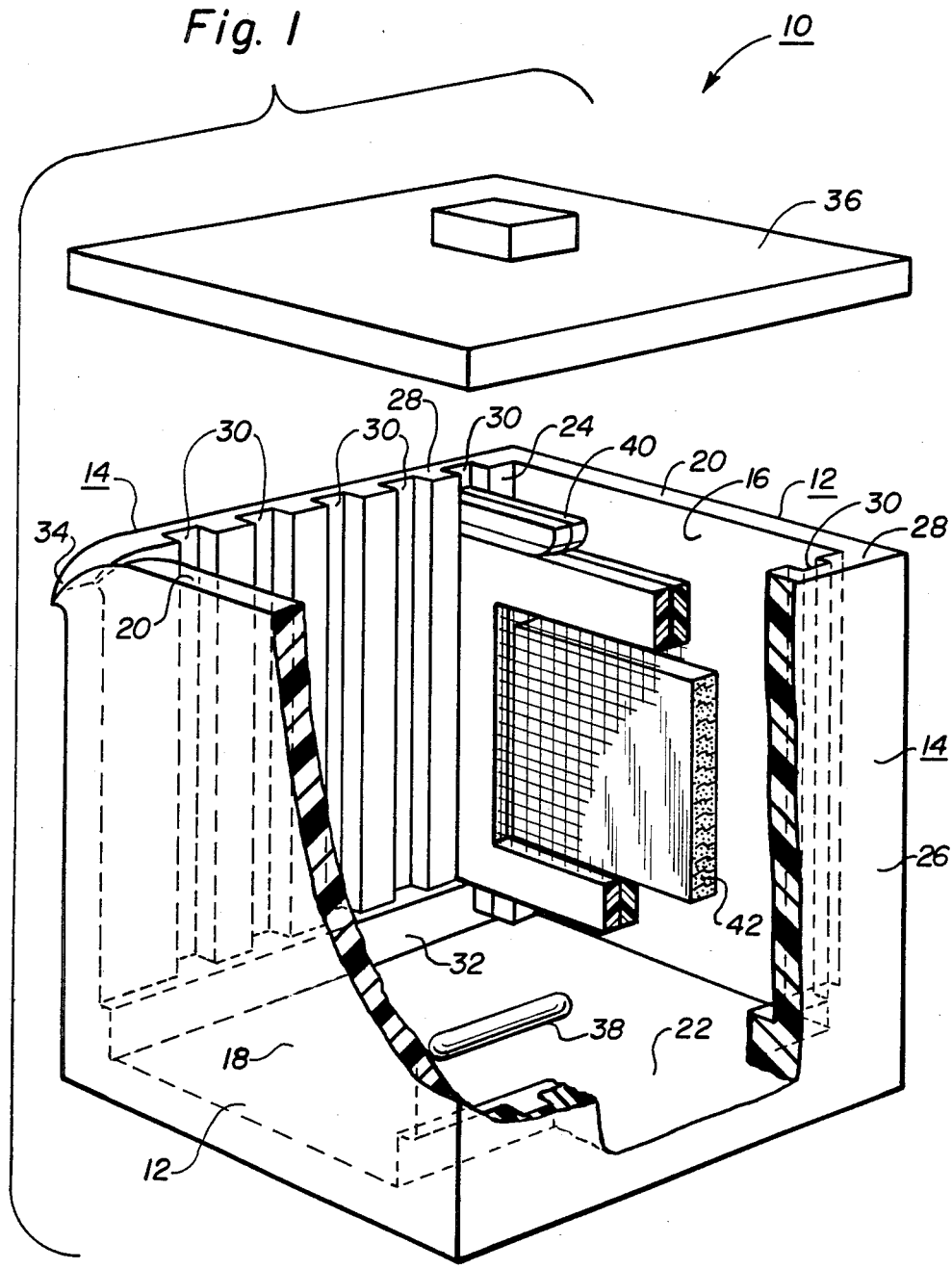
FIG. 1 is a partially broken-away perspective view of a preferred embodiment of a novel staining and destaining apparatus.

As shown in FIG. 1, the apparatus comprises a substantially retangular, liquid impermeable container 10 having a first pair of oppositely disposed sidewalls 12 and a second pair of oppositely disposed sidewalls 14. Each sidewall of the first pair of sidewalls 12 has an interior surface 16, an exterior surface 18, a top surface 20 and a bottom surface (not shown) which is attached to a bottom wall 22. Each sidewall of the second pair of sidewalls 14 has an interior surface 24, an exterior surface 26, a top surface 28 and a bottom surface (not shown) which also is attached to the bottom wall 22. A plurality of substantially parallel channels 30 are formed in the interior surface 24 of the second pair of oppositely disposed sidewalls 14. The channels 30 are preferably vertically oriented and mutually aligned, that is, the channels formed in one of the sidewall 14 are directly opposite from the channels 30 formed in the facing sidewall. The channels 30 extend from the top surface 28 of the second pair of sidewalls 14 to a stop 32 formed adjacent to the bottom surface or end thereof. Alternatively, the channels may be formed at an acute angle relative to the stop 32. Additionally, a pair of handles (not shown) may be added to the exterior surface of the container to facilitate handling. At least one pour spout 34 is formed near the top surfaces 20 and 28 of the intersecting sidewalls of the pairs of first and second sidewalls 12 and 14, respectively. Alternatively the pour spout may be formed through any of the sidewalls near the top surfaces thereof. A removable top 36 which telescopes over the top surfaces 20 and 28 of the pairs of sidewalls 12 and 14 is also provided. A magnetic stirring bar 38, shown schematically as being placed on the bottom wall 22 of the container 10, is desirable but not necessary. To activate the stirring bar the container is placed onto a stir device as is known in the art. The container 10 and the top 36 are formed, preferably by molding, from a suitable acid-resistant material such as polyvinyl chloride or polymethylpentene or an equivalent material.

A novel cassette 40 is shown in FIGS. 1-5. The cassette 40 is designed to retain a slab gel 42 or a packet 44 of a destaining material as described hereinafter. As shown in FIG. 1, the container 10 accommodates a plurality of cassettes 40 within the channels 30; although, for the purpose of illustration only one cassette is shown. In order to avoid cluttering FIG. 1, the container 10 is shown to accommodate only five cassettes; however, this is not intended to be a limitation of the invention and a greater or lesser number of channels 30 may be provided to accommodate any reasonable number of cassettes. The stops 32 provide a space between the bottom surface of the cassette 40 and the stirring device 38 and permit circulation of a gel-processing liquid.

Figure 3:
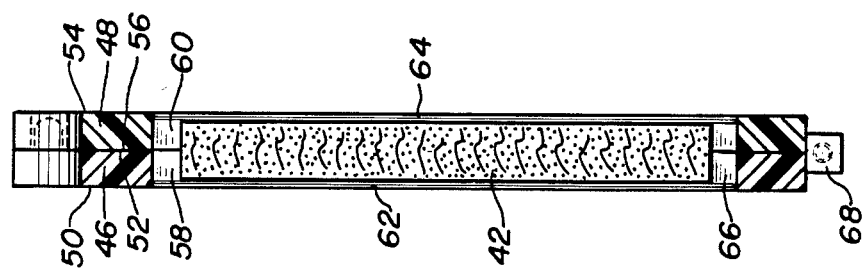
FIG. 3 is a sectional view taken along line 3-3 of FIG. 2.
Figure 2:
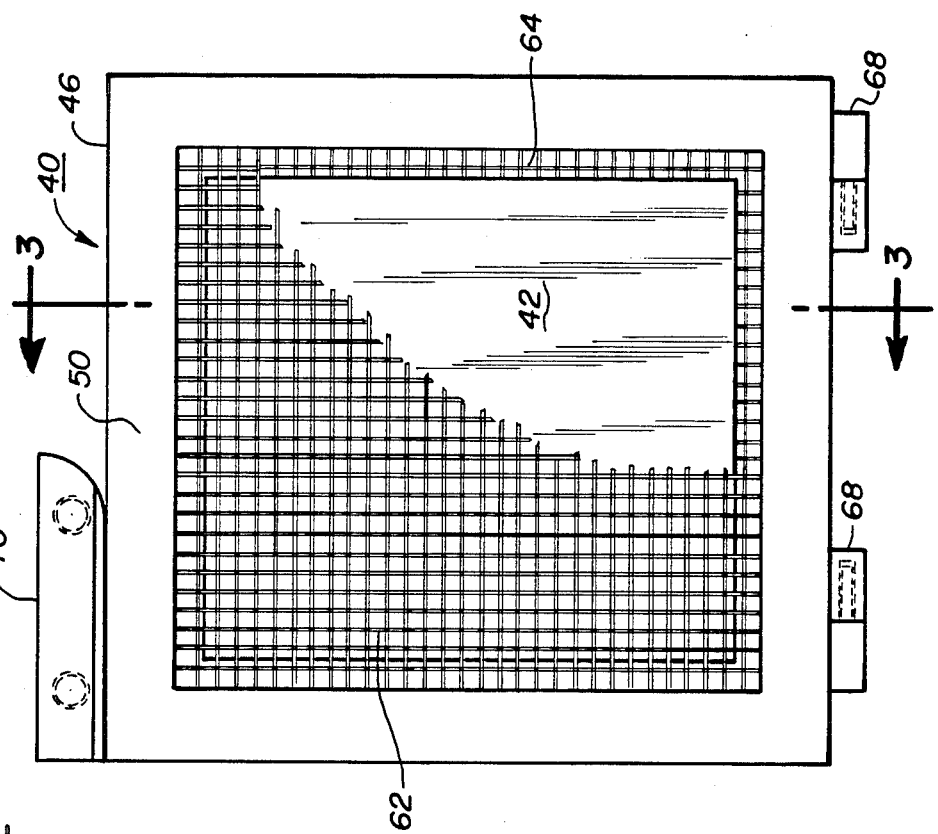
FIG. 2 is a partially broken-away plan view of a novel cassette retaining a slab gel according to the present invention.

As shown in FIGS. 2 and 3, the cassette 40 comprises a first support plate 46 and a second support plate 48. The first support plate 46 has a first major surface 50 and an oppositely disposed second major surface 52. The second support plate 48 has a first major surface 54 and an oppositely disposed second major surface 56. The first and second support plates 46 and 48 are arranged in face-to-face relation so that the second major surfaces 52 and 56, respectively, are adjacent to one another. A centrally disposed first plate recess 58 is formed in the first support plate 46 and a corresponding centrally disposed second plate recess 60 is formed in the second support plate 48. A first flexible, liquid permeable membrane or mesh 62 is integral with the first major surface 50 of the first support plate 46. The first mesh 62 extends across the first plate recess 58. A second flexible, liquid permeable membrane or mesh 64 is similarly integral with the first major surface 54 of the second support plate 48 and extends across the second plate recess 60. When the first and second support plates 46 and 48 are attached together a gel retaining chamber 66 is formed in the volume defined by the first and second meshes plate recesses 58 and 60 and the first and second meshes 62 and 64. The slab gel 42 is retained within the chamber 66 without being squeezed or otherwise damaged by the meshes 62 and 64. Preferably, the meshes 62 and 64 are formed of a plastic material which can be easily attached to or formed integral with the support plate 46 and 48 which are preferably made of polypropylene, polyvinyl chloride or similar material and which are resistant to the gel-processing liquids. To facilitate loading and unloading of the cassette 40 at least one hinge 68 and preferably two hinges is provided at one end of the support plates 46 and 48. A snap lock 70 is provided at an opposite end to detachably attached the plates 46 and 48 together. The snap lock 70 also serves as a handle for the cassette 40.

GENERAL CONSIDERATIONS

Most commerical electrophoresis systems use slab gels having transverse dimensions of 14 cm × 16 cm and thicknesses ranging from 0.4 mm to 3.0 mm. For slab gels of this size a container 10 having a first pair of sidewalls 12 with a length of 21 cm and a height of 30 cm and having a second pair of sidewalls 14 with a length of 22 cm and a height of 30 cm would provide a container having outside dimensions of 21 cm × 22 cm × 30 cm. Typically, the thickness of the sidewalls is in the range of about 1.0 to 1.5 cm. The channels 30 are about 1.0 cm wide and there is a space of about 2.0 cm between adjacent channels. The stops 32 extend about 3 cm above the bottom surface of the sidewalls 14. The cassette 40, designed to hold the 14 cm × 16 cm gel slab 42, is formed from first and second support plates 46 and 48 each having a thickness of about 0.5 cm. Excluding the snap 70 and the hinges 68, the cassette 40 has a height of about 24 cm and a width of about 20 cm. The plate recesses 58 and 60 are substantially rectangular and are about 18 cm in height and 16 cm wide. Typically, the snap lock 70 extends about 2 cm above the cassette 40.

The container 10 and the cassette 40 may also be scaled down in size to run mini gel slabs which range from about 8 cm × 8 cm to about 10 cm × 10 cm in transverse dimensions and have thicknesses in the range of 0.4 mm to 0.8 mm, or scaled up in size to run larger gel slabs which range from 16 cm × 20 cm to about 16 cm × 40 cm with thicknesses ranging from 0.4 mm to 3.0 mm.

The primary advantage of the present apparatus over prior systems is that after electrophoresis has been run on the slab gels, the staining and destaining of the slab gels can be accomplished with a minimum amount of handling of the gels and within the same container. Alternatively, one container can be used for staining and a second container can be used for destaining.

STAINING

The container 10 is filled to a suitable height with a stain solution containing about 0.05% Coomassie Blue stain, 10% acetic acid and 10% butanol, methanol or isopropanol. A slab gel 42, after electrophoresis, is placed within the gel retaining recess 66 of a cassette 40 and loaded into the container 10 by placing the cassette 40 into one of the facing pairs of channels 30. By way of example, if the container 10 can accommodate five cassettes, four cassettes are loaded with slab gels and placed in the container. The stain solution should cover the slab gels but not the snap locks 70 which also serve as the handles. The stain is allowed to incubate in the closed container 10 at room temperature for several hours or overnight, depending on the thickness of the gels. The stirring device 38 may be activated to gently swirl and circulate the stain solution.

DESTAINING

Without removing the cassette 40 from the container 10, the stain solution may be poured off by means of the pour spout 34 and the container 10, with the cassettes 40 therein, is gently rinsed with water to remove the excess stain from the slab gells 42. The water is removed, and a 10% acetic acid solution is added to the container 10 to a height just below the snap locks 70 of the cassette 40. To faciliate removing stain from the destaining solution, a cassette 40 containing a packet 44 (shown in FIGS. 4 and 5) of a suitable destaining material, such as charcoal, may be added to one of the vacant pair of channels 30. The charcoal is held within a liquid permeable material such as nylon, polyester or cotton. The top 36 is placed on the container 10 and the stirring device 38 is activated to circulate the destaining solution. The progress of the destaining process can readily be monitored simply by raising each of the cassettes 40 in the channels 30 until the slab gel 42 is visible through the meshes 62 or 64. When destaining is complete, that is when the ionic bands are clearly visible and the background stain is removed, the cassettes 40 can be removed from the container 10 and the slab gel can be photographed as described hereinafter. After photographing, the slab gel 42 is returned to the cassette 40 and immersed in yet another container 10 filled with a shrinking solution of polyethylene glycol and ethanol.

Alternatively, rather than pouring off the staining solution, the cassettes 40 can be removed from the container 10, which is used as a stain tank, and the cassettes may be gently rinsed in water and then placed in a separate container 10 which acts as a destaining tank. This latter process allows for the reuse of staining and destaining solutions by the use of two separate containers 10, a suitable number of cassettes 40 and destaining packets 44.

PHOTOGRAPHIC PLATE

After the cassette 40 is removed from the container 10 which holds the destaining solution, the gel slab can be placed on a gel photographic plate 84, such as that shown in FIGS. 6 and 7, and photographed with transmitted light. The gel photographic plate 84 comprises a substantially flat, transparent viewing plate 86 of, for example, optical quality glass, surrounded by a peripheral rim portion 88 which extends above the viewing plate and retains and aligns the gel slab (not shown). The rim portion 88 holds, within its confines, a sufficient amount of liquid such as 10% acetic acid to keep the gel moist and flat. Measuring indicia 90 are provided on the viewing plate 86, for example by etching or scribing lines therein. The measuring indicia 90 provide a scale for measuring the relative position of the visible (stained) components in the slab gel.

What is claimed is:

1. An apparatus for processing a slab gel comprising a liquid impermeable enclosure having a bottom, sidewalls attached to said bottom and a top, said sidewalls including a plurality of indexing means formed on two opposite sidewalls therein, and
at least one cassette for retaining said slab gel, said cassette being supported and disposed within said indexing means, said cassette comprising a first and a second support plate, each of said support plates having a first and a second major surface, said support plates being arranged so that said second major surface of said first support plate is adjacent to said second major surface of said second support plate, each of said support plates having a recess therein, said first major surface of each of said support plates having a liquid permeable membrane extending across said recess so as to form a slab retaining chamber therebetween, and attachment means for securing said first support plate to said second support plate.

2. The apparatus as described in claim 1 wherein said top is removable.

3. The apparatus as described in claim 1 wherein said indexing means includes a plurality of channels formed in said sidewalls.

4. The apparatus as described in claim 1 wherein said liquid permeable membrane comprised a mesh.

5. The apparatus as described in claim 1 wherein said attachment means comprises at least one hinge and at least one lock.

6. The apparatus as described in claim 1 further including a pour lip in said sidewall portion of said enclosure.

7. An apparatus for staining and destaining electrophoresis slab gels utilizing a suitable staining or destaining liquid, said apparatus comprising
a substantially rectangular, liquid impermeable container having two pairs of oppositely disposed sidewalls, a bottom wall attached to said sidewalls and a top, a plurality of substantially parallel channels being formed in an interior surface of one of said pairs of oppositely disposed sidewalls, said channels extending from a top end of said one pair of sidewalls to stops formed in a bottom end thereof, said channels in said one pair of oppositely disposed sidewalls being mutually aligned, and
a plurality of cassettes for retaining said slab gels each of said cassettes being supported and disposed within one of said channels, each of said cassettes comprising a first and a second support plate, each of said support plates being arranged in face-to-face relation so that said second major surface of said first support plate is adjacent to said second major surface of said second support plate, each of said support plates having a centrally disposed recess therein, said first major surface of each of said support plates having a mesh extending across said centrally disposed recess so as to form a gel retaining chamber therebetween, saif first and second support plates being attached together at one end by at least one hinge and being detachably attached together at an opposite end by at least one snap lock.

8. The apparatus as described in claim 8 wherein a pouring lip is formed in said sidewall.

9. A destainer for electrophoresis slab gels utilizing a suitable destaining solution, said destainer comprising
a substantially rectangular, liquid impermeable container having two pairs of oppositely disposed sidewalls, a bottom wall attached to said sidewalls, and a top, a plurality of substantially parallel channels being formed in an interior surface of one of said pairs of oppositely disposed sidewalls, said channels extending from a top end of said one pair of sidewalls to stops formed in a bottom end thereof, said channels in said one pair of oppositely disposed sidewalls being mutually aligned,
a plurality of cassettes disposed within different ones of said mutually aligned channels, each of said cassettes comprising substantially rectangular first and second support plates, each of said plates having a first and second major surfaces, said support plates being arranged in face-to-face relation so that said second major surface of said first support plate is adjacent to said second major surface of said second support plate, each of said support plates having a centrally disposed, substantially rectangular recess therein, said first major surface of each of said support plates having a mesh integral therewith and extending across said central recess os as to form a chamber therebetween, said first and second plates being attached together at one end by at least one hinge and detachably attached together at an opposite end by at least one snap lock, and destaining means disposed within said recess in at least one of said cassettes for removing stain from said destaining solution.

10. The destainer as described in claim 9 wherein said top is removable.

11. The destainer as described in claim 9 wherein a pour lip is formed in said sidewall.

12. The destainer as described in claim 9 wherein said destaining means comprises a packet of a stain absorbing material.

13. The destainer as described in claim 12 wherein said packet comprises a liquid permeable material for containing said stain absorbing material.

14. The destainer as described in claim 13 wherein said liquid permeable material is selected from the group consisting of nylon, polyester and cotton.

* * * * *